(12) United States Patent
Chitwood et al.

(10) Patent No.: US 7,597,673 B2
(45) Date of Patent: Oct. 6, 2009

(54) HIGH GRIPPING AND NON-SLIP BELTS FOR PNEUMATIC LUMBAR TRACTION DEVICE

(75) Inventors: Nathan Chitwood, Kalispell, MT (US); Susan Nickell, Kalispell, MT (US)

(73) Assignee: Glacier Cross, Inc., Kalispell, MT (US)

( * ) Notice: Subject to any disclaimer, the term of this patent is extended or adjusted under 35 U.S.C. 154(b) by 195 days.

(21) Appl. No.: 11/973,107

(22) Filed: Oct. 5, 2007

(65) Prior Publication Data

US 2009/0093745 A1 Apr. 9, 2009

(51) Int. Cl.
*A61F 5/00* (2006.01)

(52) U.S. Cl. .............................. 602/19; 602/32; 602/35; 602/36

(58) Field of Classification Search .................. 602/19, 602/32, 35, 36; 128/869, 874; 2/311, 312, 2/321, 322
See application file for complete search history.

(56) References Cited

U.S. PATENT DOCUMENTS

| | | | |
|---|---|---|---|
| 3,888,245 A * | 6/1975 | Berntson et al. ............... 602/19 |
| 3,960,146 A | 6/1976 | Albrecht |
| 4,073,290 A | 2/1978 | Farrar, Jr. |
| 4,099,523 A | 7/1978 | Lowrey |
| 4,135,503 A | 1/1979 | Romano |
| 4,356,816 A | 11/1982 | Granberg |
| 4,466,427 A | 8/1984 | Granberg |
| 4,508,109 A | 4/1985 | Saunders |
| 4,627,423 A | 12/1986 | Kampner |
| 4,641,637 A | 2/1987 | Rosen |
| 4,664,101 A | 5/1987 | Granberg |
| 4,665,908 A * | 5/1987 | Calkin ......................... 128/870 |
| 4,995,378 A | 2/1991 | Dyer et al. |
| 5,052,378 A | 10/1991 | Chitwood |
| 5,115,802 A | 5/1992 | Dyer |
| 5,363,863 A * | 11/1994 | Lelli et al. ................... 128/876 |
| 5,667,529 A | 9/1997 | Butner |
| 6,009,839 A * | 1/2000 | Kohn .......................... 119/770 |
| 6,045,525 A | 4/2000 | Chitwood |
| 6,240,923 B1 * | 6/2001 | Barrick ........................ 128/869 |
| 6,610,022 B1 * | 8/2003 | Ashbaugh et al. .............. 602/19 |
| 7,108,671 B2 | 9/2006 | Saunders et al. |

* cited by examiner

*Primary Examiner*—Michael A. Brown
(74) *Attorney, Agent, or Firm*—Thomas R. Vigil

(57) ABSTRACT

The pneumatic lumbar traction device comprises two separable parts, namely an upper hollow part and a lower frame, the frame having a pneumatically operated piston and cylinder mechanism fixed in and located centrally therein with a piston rod extending outwardly to engage a bar positioned to engage and move a loop fixed to a pelvic traction belt outwardly of a foot end of the device; the upper hollow part having an upper surface on which a user will lie during use; a generally elongate chest belt having opposite end portions with a strap fixed on each end portion with a first clip on said strap and a mating second clip fixed on the opposite end portion, each strap, after said mating clips are fixed together, being capable of being pulled through said first clip to tighten it on the first clip against said fixed mating second clip thereby to tighten the chest belt around a users chest; two, spaced apart, elongate strips of hook or loop material fixed to a central area of the upper surface for engaging with an outer surface of the chest belt for fixing the chest belt to the upper surface.

44 Claims, 5 Drawing Sheets

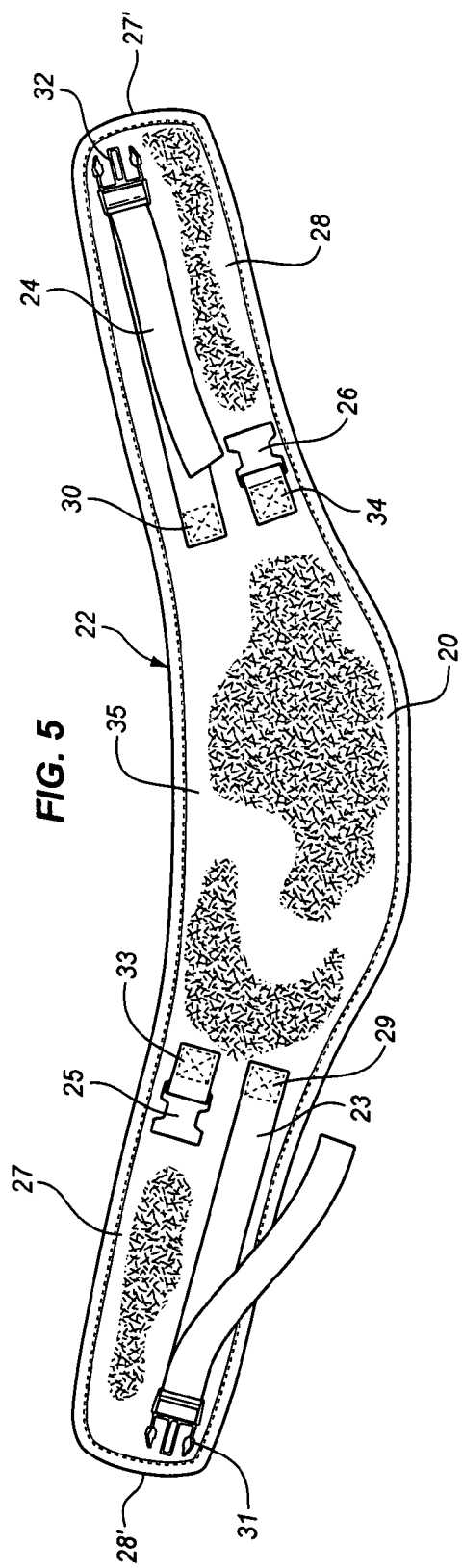
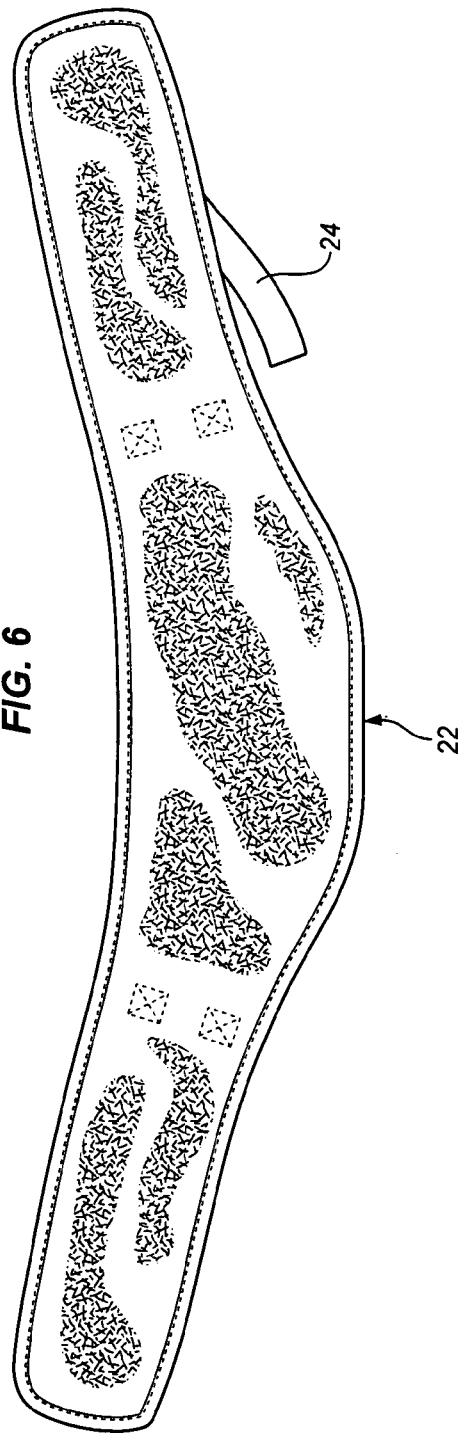
FIG. 5
FIG. 6

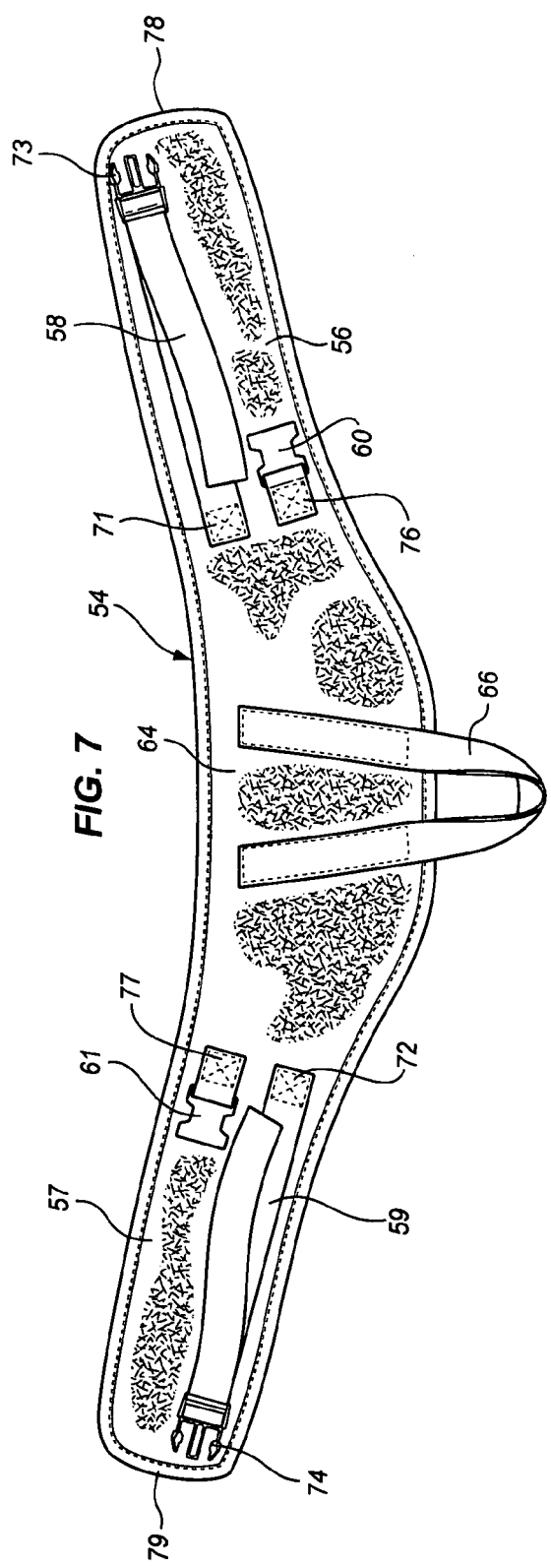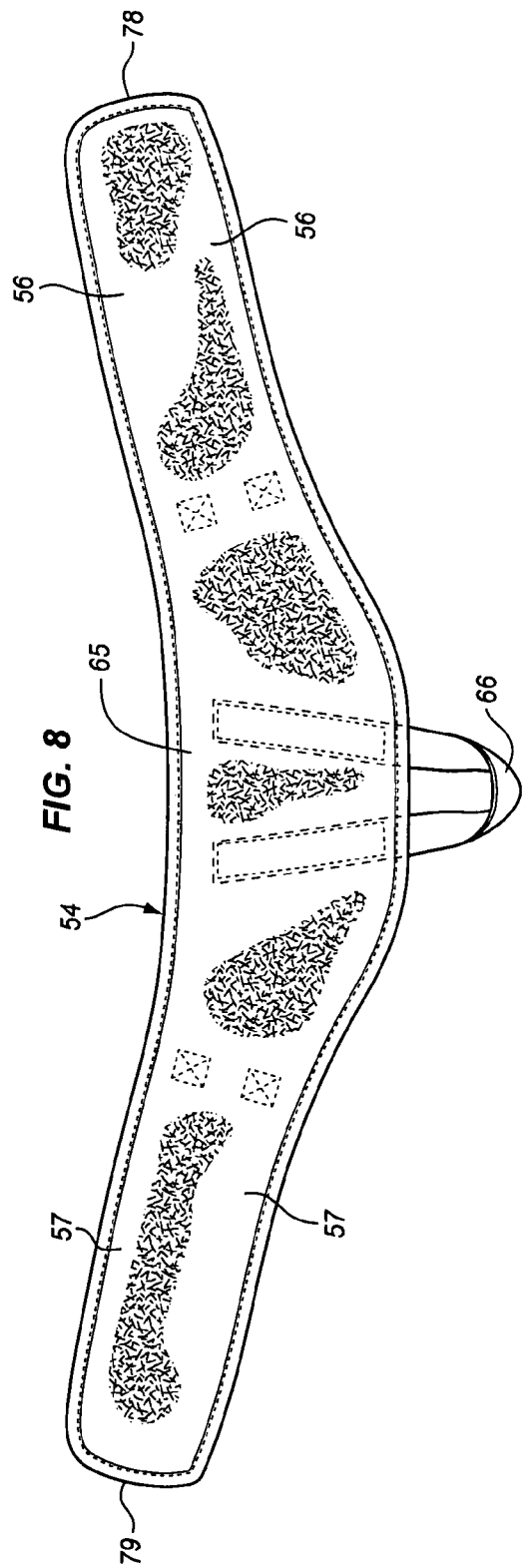

HIGH GRIPPING AND NON-SLIP BELTS FOR PNEUMATIC LUMBAR TRACTION DEVICE

BACKGROUND OF THE INVENTION

1. Field of the Invention

The present invention relates to a pneumatic lumbar traction device which can be placed on the floor or any other horizontal surface, such as a table, and the user thereof can strap himself or herself to an upper surface of the device and then, by pumping a hand pump, can cause a lower pelvic traction belt strapped around the pelvic area of a body to be pulled outwardly from a foot end of the device with a chest belt fixed on the chest of the body holding the user to the upper surface of the device. More specifically, the present invention relates to improved pelvic and chest belts which improve fixing of the belts on the body to minimize slippage of the belts on the body and improve traction on the body with lubricious material on the outer surface of the pelvic traction belt to enhance sliding of the pelvic traction belt on the upper surface of the device.

2. Description of the Prior Art

Heretofore various traction belts and traction devices have been proposed where a user can exert a stretching force on the lumbar area of the back. Examples of previously proposed traction belts and traction devices are disclosed in the following U.S. patents.

| U.S. Pat. No. | Patentee |
|---|---|
| 3,960,146 | Albrecht |
| 4,073,290 | Farrar, Jr. |
| 4,099,523 | Lowrey |
| 4,135,503 | Romano |
| 4,356,816 | Granberg |
| 4,466,427 | Granberg |
| 4,508,109 | Saunders |
| 4,627,423 | Kampner |
| 4,641,637 | Rosen |
| 4,664,101 | Granberg |
| 4,995,378 | Dyer et al. |
| 5,052,378 | Chitwood |
| 5,115,802 | Dyer |
| 5,667,529 | Butner |
| 6,045,525 | Chitwood |
| 7,108,671 | Saunders et al. |

These prior art lumbar traction devices used wide belts which are fixed around a body using hook and loop fastening material sold under the trademark VELCRO®. The thinking at the time of the invention of these lumbar traction devices was to use a simple fastening structure, e.g., VELCRO® between the end portions of the belts or straps. While this worked well, there was still slippage of the belts or straps on the torso of the body which reduced the effectiveness of the stretching of the lumbar area.

As will be described in greater detail hereinafter, the pneumatic lumbar traction device of the present invention differs from the various devices disclosed in the prior art patents and literature described above by providing a pelvic belt and a chest belt which are fastened about and fixed to a body with two pairs of straps and male and female clips or buckles.

For years, the simplicity of hook and loop fastening structure on chest belts and pelvic traction belts in lumbar traction devices has overlooked the slippage of such belts because of their inability to effect sufficient tightness of the belts around a user's body. Through trial and error, applicants have determined that the use of a pair of straps on each belt fixed together with male and female clips (like on airplane seatbelt buckles) on each belt where each strap can be tightened against fixed male and female clips and provides much more tightness of the belts around a user's body resulting in much better lumbar/back/spinal stretching.

SUMMARY OF THE INVENTION

According to the present invention there is provided a pneumatic lumbar traction device of the type disclosed in the Chitwood U.S. Pat. No. 6,045,525 which has an upper smooth surface on which a user will lie, the improvement residing in a chest belt having a pair of straps and clips or buckles for fixing the belt around the chest of a body. The outer surface of the chest belt has hook or loop material for fixing the chest belt to two elongate spaced apart strips of loop or hook material fixed on and to the upper smooth surface of the device. The chest belt has opposite end portions with two first straps fixed on each end portion with a male clip or female clip slidable on the strap and received around a bar in a transverse slot in the clip and an opposed second short strap or tab on the opposite end portion with a female or male clip at an outer end thereof and the first strap can be pulled around the bar in the transverse slot in the first named clip, after the opposed clips are fixed together, thereby to tighten the chest belt around a users chest. The improvement also resides in a pelvic traction belt that is adapted to be received around the pelvic area of a user and has a loop fixed thereto and extending outwardly transversely of the pelvic traction belt toward a foot end of the device and the belt having opposite end portions with two first straps fixed on each end portion with a male clip or female clip slidable on the strap and received around a bar in a transverse slot in the clip and an opposed second short strap or tab on the opposite end portion with a female or male clip at an outer end thereof and the first strap can be pulled around the bar in the transverse slot in the first named clip, after the opposed clips are fixed together, to thereby the pelvic traction belt around a users pelvic area and with the outer surface of the pelvic belt being made of a low friction lubricious material to facilitate sliding of the pelvic traction belt on the smooth upper surface of the lumbar traction device. The loop is adapted to be fixed on a bar or lug at the end of a piston rod extending from a pneumatic piston and cylinder mechanism which is actuated by a hand pump to pull the pelvic area from the chest area of the user to exert traction on the lumbar area of the user.

BRIEF DESCRIPTION OF THE DRAWINGS

FIG. 5 is a bottom plan view of the chest belt shown in FIG. 1.

FIG. 6 is a top plan view of the chest belt shown in FIG. 5.

FIG. 7 is a bottom plan view pelvic traction belt shown in FIG. 1.

FIG. 8 is a top plan view of the pelvic traction belt shown in FIG. 7.

DESCRIPTION OF THE PREFERRED EMBODIMENT(S)

Figure 1:
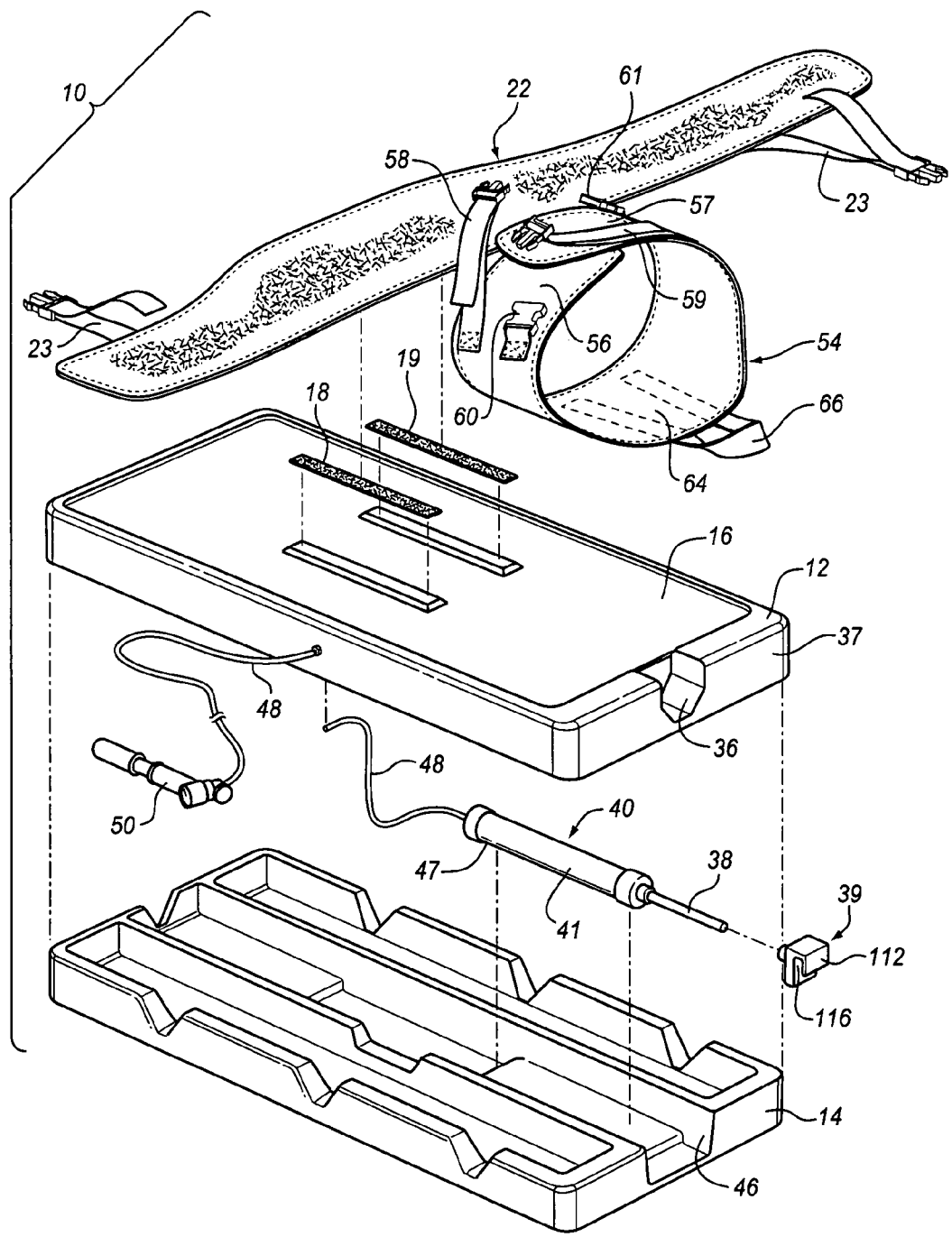
FIG. 1 is an exploded perspective view of the pneumatic lumbar traction device including an upper, hollow shell part, a lower plate part mounting a pneumatic piston and cylinder mechanism, a chest belt and a pelvic traction belt constructed according to the teachings of the present invention.

Referring now to the drawings in greater detail, there is illustrated in FIG. 1 a pneumatic lumbar traction device 10 constructed according to the teachings of the present invention. The device 10 includes an upper, hollow shell part 12 and a lower board, plate or framework part 14.

The upper, hollow shell part 12 is generally rectangular and constructed and arranged to fit over the lower plate part 14 and has an upper surface 16 which can be a slippery surface, such as by being coated with a lubricous material, i.e., with Teflon®.

It is important to note that on the upper surface 16 there are provided two elongate patches 18 and 19 of hook material sold under the trademark Velcro®. The patches 18 and 19 are adapted to engage with loop fabric material 20 on the outside of a chest belt 22 for holding the chest belt 22 to the upper surface 16 of the upper, hollow shell part 12.

As will be described in detail hereinafter in connection with the description of FIGS. 5 and 6, the chest belt 22 further has a pair of straps 23 and 24, spaced apart in the elongate direction of the belt 22, and a pair of buckles or female clips 25 and 26, spaced apart in the elongate direction of the belt 22. One strap 23 and one male clip 25 are fixed on the surface 20 on one end portion 27 of the belt 22 and the other strap 24 and the other female clip 26 are fixed on the surface 20 on the other end portion 28 of the chest belt 22 for enabling a tight and secure fastening of the chest belt 22 around the chest of a user.

The end portions 27 and 28 shown in FIGS. 5 and 6, have a length between 8 and 12 inches, preferably about 11 inches. The overall length of the chest belt 22 is between 46 and 52 inches, and preferably about 50 inches. The width of the end portions 27 and 28 is between 5 and 7 inches, and preferably 6 inches.

Each strap 23 or 24 has an inner end 29 or 30 that is fixed, such as by stitching to the chest belt 22. Also, each strap 23, 24 has a male clip 31 or 32 fixed to the outer end thereof for being clipped in one of the female clips 25 or 26. The female clips 25, 26 are mounted to rectangular tabs 33 or 34 which are fixed, such as by stitching, to the chest belt 22.

The straps 23 and 24 have a length of between 13 and 20 inches, preferably between 15 and 18 inches from the inner end 29 or 30 to the male clip and are adjustably fixed in a particular position, like in an airplane seat belt clip.

The inner edge of each tab 33 or 34 is fixed to an outer surface of the end portion 27 or 28. The distance between the tab 33 or 34 and the outer end 27' or 28' of the end portions 27 and 28 is between 15 and 17 inches, and preferably about 16 inches. The width of each strap 23, 24 and tab 33, 34 is between 1 and 2 inches, preferably about 1.5 inches wide with a spacing between them of between 1 and 2 inches, preferably about 1.5 inches.

Finally, the chest belt 22 has a mid portion 35 having a width between 8 and 10 inches, preferably about 9 inches wide.

As shown, the upper, hollow shell part 12 has an opening 36 at a foot end 37 of the upper, hollow shell part 12 through which a guided bar/piston rod 38 can extend for connection to a T-bar 39.

The lower plate part 14 comprises a generally rectangularly shaped board, plate or frame having centrally mounted thereon, a pneumatic piston and cylinder mechanism 40 comprising a cylinder 41 and a piston (hidden from view) which acts upon the guided bar/piston rod 38 extending outwardly out of the piston and cylinder mechanism 40 for engagement with the T-bar 39.

A track or guideway 46 is formed on the board or plate 14 for holding the guided bar/piston rod 38 against lateral movement during use of the device 10.

Extending from an inner end 47 of cylinder 40 is a tubing 48 which extends to a hand pump 50 and an air gauge 52. The pump 50 can be of any suitable construction such as a cylindrical air pump as shown, or a T handle bicycle tire pump, or it can be a bulb type pump with a check valve, as is known in the art.

The pneumatic lumbar traction device 10 further includes a pelvic traction belt 54, as shown in FIGS. 1, 7 and 8, including end portions 56 and 57 each having on the bottom surface thereof a pair of spaced apart straps 58 and 59 and a pair of spaced apart female clips or buckles 60 and 61.

As shown in FIG. 8, the pelvic traction belt 54 has a central body portion 64. Then, extending from a bottom side 65 of the central body portion 64 of the pelvic traction belt 54 is a loop 66 which is adapted to be connected to the T-bar 39. The loop 66 has a bight portion which is received around the T-bar 39.

If desired, the outer surface of the pelvic traction belt 54 can be coated with or made from a lubricous material, such as polytetraflourethylene, commonly sold under the trademark Teflon® to facilitate sliding of the user and the pelvic traction belt 54 on the upper surface 16 of the upper part 12.

Note that the loop 66 is mounted to the bottom side 65 of the pelvic traction belt to prevent the loop 66 from irritating the user. Also note, from FIGS. 2 and 3, that the thighs of the user extend 900 upward from the horizontal and the feet of a user rest on a raised foot support 68 such that loop 66 does not impede sliding movement of the user's pelvis on the upper surface 16.

Figure 2:
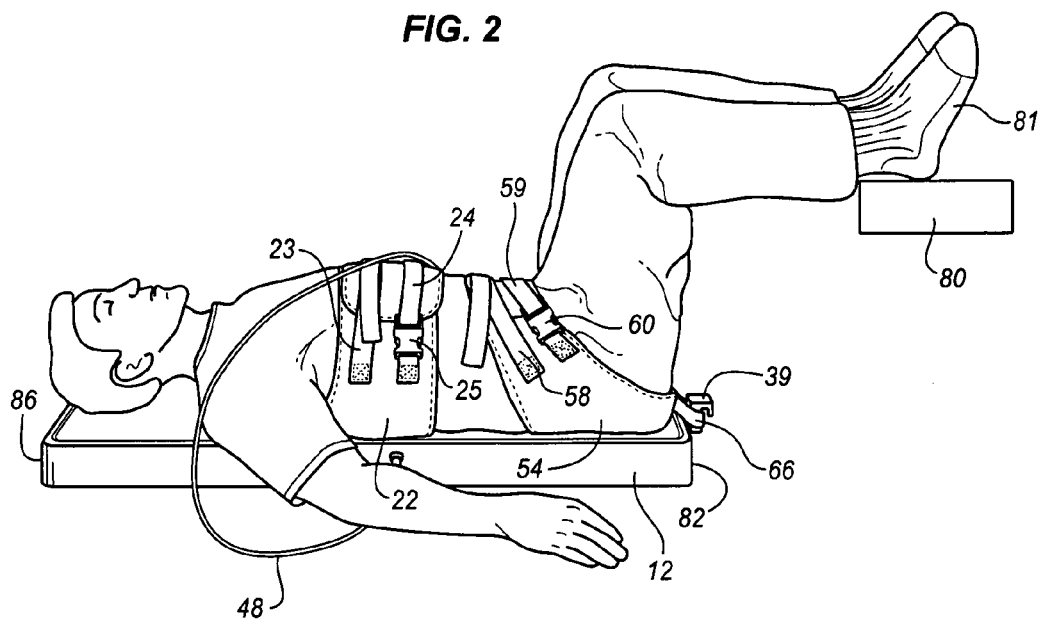
FIG. 2 is a side elevational view of the device shown in FIG. 1 with a user resting on the device.
Figure 3:
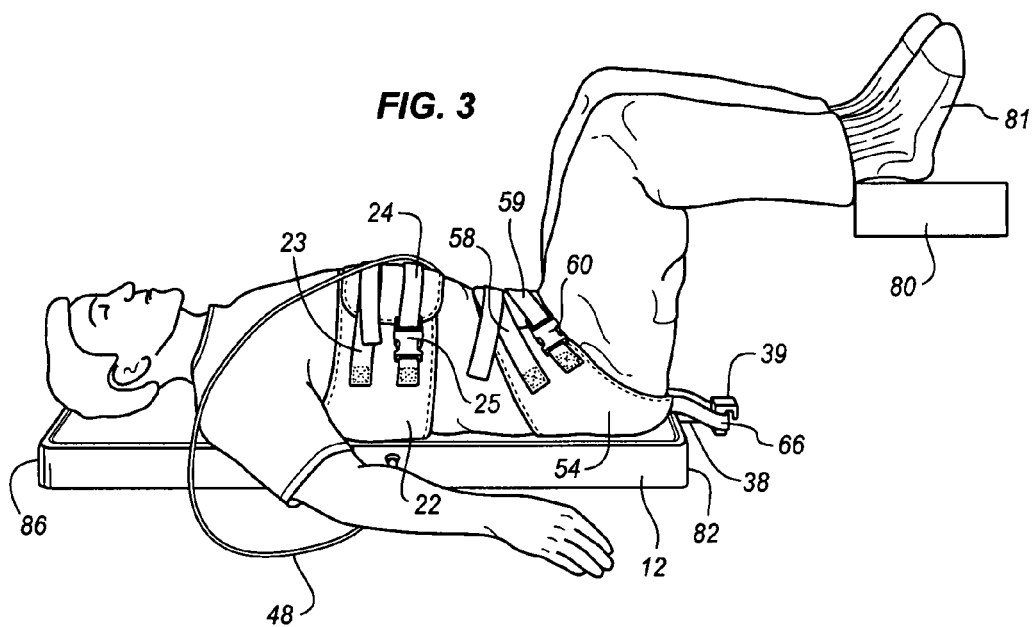
FIG. 3 is a side elevational view of the device, similar to the view shown in FIG. 2, but showing a loop of the pelvic traction belt connected to a bar or lug that is connected to a piston rod extending from the piston and cylinder mechanism and which extends from a foot end of the device.
Figure 4:
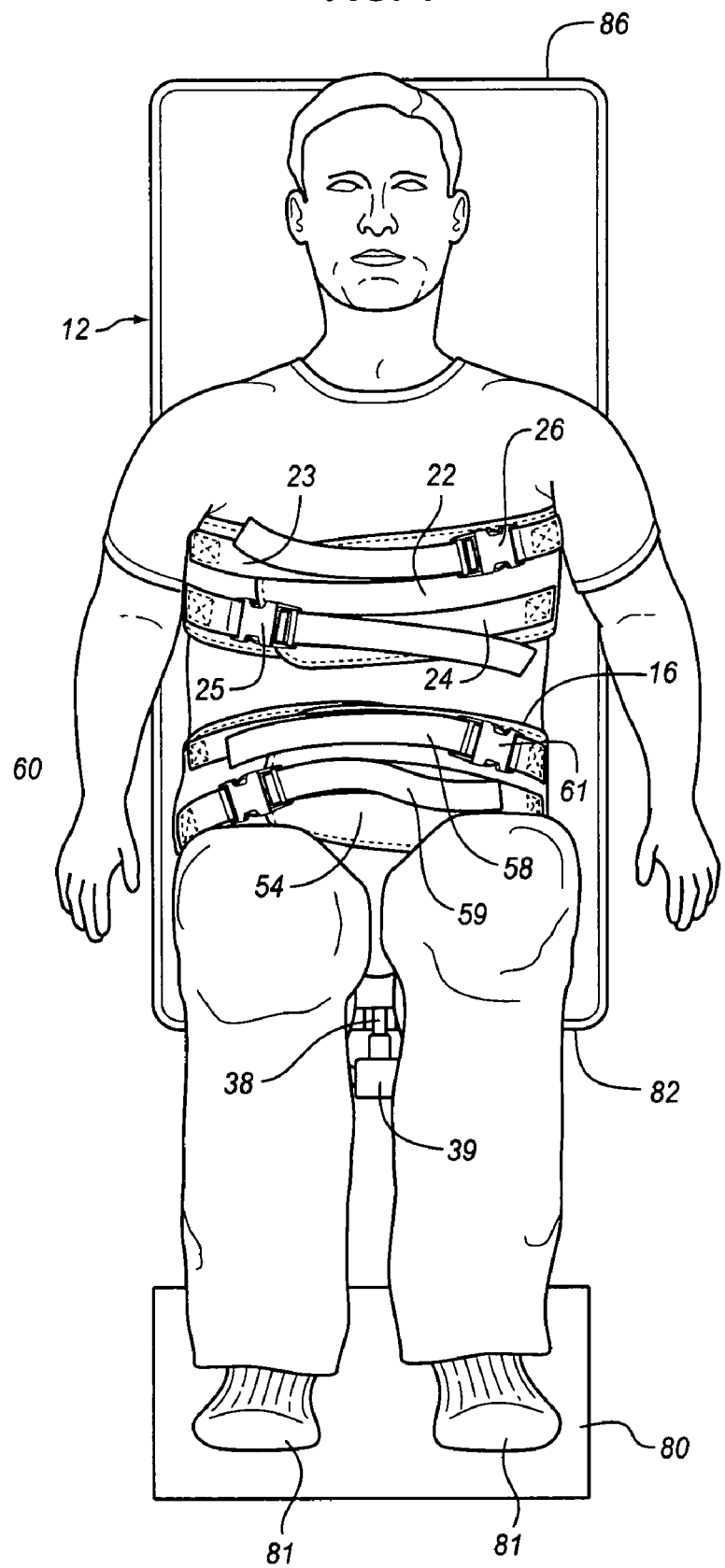
FIG. 4 is a top plan view of the user and the device shown in FIG. 3.

Further note that the raised foot support 68, such as a chair seat or a raised foot rest 80 supports the feet 81 of a user with the user's knees bent 90° as best shown in FIGS. 2, 3 and 4.

Returning to FIGS. 7 and 8, the end portions 56 and 57 have a length between 8 and 12 inches, preferably about 11 inches. The overall length of the pelvic traction belt 54 is between 46 and 52 inches, preferably about 50 inches. The width of the end portions 56 and 57 is between 5 and 7 inches, preferably 6 inches.

Each strap 58 or 59 has an inner end 71 or 72 which is fixed, such as by stitching to the pelvic traction belt 54. Also, each strap 58, 59 has a male clip 73 or 74 fixed to an outer end thereof for being clipped into one of the female clips 60 or 61. The female clips 60, 61 are mounted to rectangular tabs 76 or 77 which are fixed, such as by stitching, to the pelvic traction belt 54.

The straps 58 and 59 have a length of between 13 and 20 inches, preferably 15 to 18 inches from the inner end 71 or 72 to the male clip 60 or 61 and are adjustably fixed in a particular position, like an airplane seat belt.

The inner edge of each tab 76, 77 to an outer edge 78, 79 of the end portion 56 or 57 is between 15 and 17 inches, preferably about 16 inches. The width of each strap 58, 59 and tab 76, 77 is between 1 and 2 inches, preferably about 1.5 inches wide with a spacing between them of between 1 and 2 inches, preferably about 1.5 inches.

Finally, the pelvic traction belt 22 has the mid portion 64 having a width between 8 and 10 inches, preferably about 9 inches wide.

The chest belt 22 and pelvic traction belt 54 are made by a flame lamination process with loop 3610 knitted nylon, hook compatible fabric and loop 3900 brushed nylon, hook compatible fabric, black polyurethane foam, starting thickness 0.090 and latex free.

From the foregoing description, it will be appreciated that a simple improved pneumatic lumbar traction device 10 is provided where a chest belt 22 is fixed to the upper surface 16 of the hollow shell part 14 by hook and loop material, as described above, and the chest belt 22 can then be fastened tightly around the chest of a user using the pair of straps 23 and 24 with male clips 31, 32 and the female clips or buckles 25, 26 fixed with tabs to the end portions on the chest belts. Then, with the user held to the upper hollow shell part 12 by the chest belt 22, the pelvic traction belt 54 is fixed tightly around the user's pelvis using the pair of straps 58, 59 with male clips 73, 74 and female clips or buckles 60, 61 fixed to the end portions of the pelvic belt. The straps 23, 24 or 58, 59 are pulled tight after the male clips 31, 32 or 73, 74 are fixed in the female clips 25, 26 or 60, 61. The pulling of the straps 23, 24 or 58, 59 against the fastened clips 31, 32 or 73, 74 and 25, 26 or 60, 61, such as around a locking bar in a slot in the male clip (like in an airplane seat belt buckle), enables the user to obtain a tighter fixing of the belts 22 and 54 to the user's body than with belt end portions fixed together with mating hook and loop material on the end portion, thereby to provide enhanced stretching of the lumbar region.

Next, the user's pelvic area can be pulled outwardly from the foot end 82 of the device 10 for stretching and placing traction on the lumbar area of the users back with minimal or no slipping of the chest belt 22 on the chest of the user or of the pelvic traction belt 54 on the pelvis of the user.

Desirably, the upper surface 16 is inclined slightly, 1 to 15 degrees, from a foot end 82 of the device 10 to a head end 86 of the device 10, as shown in FIGS. 2 & 3, to facilitate sliding movement of the user on the upper surface 16.

Further, as best shown in FIG. 1, the T-bar 39 engages the belt loop 66 and the user, by operating the pump 50, cause the rod/piston rod 38 to push the T-bar 39 and loop 66 and pelvic traction belt 54 away from the shell part 12 to stretch the users back as shown in FIG. 3.

The male and female clips are standard 1.5 inch acetal male and female buckles distributed by Wirewright Manufacturing of Anniston, Ala.

From the foregoing description, it will be apparent that the pneumatic lumbar traction device 10 of the present invention has a number of advantages, some of which have been described above and others which are inherent in the invention, and particularly better tightening of the chest belt and the pelvic belt around the torso, thereby providing better stretching of the lumbar region.

Also from the foregoing description, it will be apparent that obvious modifications can be made to the chest belt or pelvic belt without departing from the teachings of the invention. Accordingly, the scope of the invention is only to be limited by the accompanying claims.

We claim:

1. A pneumatic lumbar traction device comprising:
    two separable parts, namely an upper hollow part and a lower frame,
    said frame having a pneumatically operated piston and cylinder mechanism fixed in and located centrally therein with a piston rod extending outwardly to engage a bar positioned to engage and move a loop fixed to a pelvic traction belt outwardly of a foot end of said device;
    said upper hollow part having an upper surface on which a user will lie during use;
    said upper surface of said upper hollow part is coated on the lower portion thereof with a lubricous material to facilitate sliding movement of the pelvic traction belt on said upper surface
    a generally elongate chest belt having opposite end portions with a strap fixed on each end portion with a first clip on said strap and a mating second clip fixed on the opposite end portion, each strap, after said mating clips are fixed together, being capable of being pulled through said first clip to tighten it on the first clip against said fixed mating second clip, thereby to tighten the chest belt around a users chest;
    two, spaced apart, elongate strips of hook or loop material fixed to a central area of said upper surface for engaging with an outer surface of said chest belt for fixing said chest belt to said upper surface; and,
    a pelvic traction belt adapted to be received around the pelvic area of a user and having said loop fixed thereto and extending outwardly transversely of the pelvic traction belt toward said foot end of said device and said pelvic traction belt having opposite end portions with a strap fixed on each end portion with a strap fixed on each end portion with a first clip on said strap and a mating second clip fixed on the opposite end portion, each strap, after said mating clips are fixed together, being capable of being pulled through said first clip thereby to tighten it on the first clip against said fixed mating second clip thereby to tighten the pelvic traction belt around a users pelvic area.

2. The pneumatic lumbar traction device of claim 1 wherein said chest belt has a loop or hook like material thereon for being releasably fixed to said elongate strips on said upper surface.

3. The pneumatic lumbar traction device of claim 1 including a hand pump coupled to said piston and cylinder mechanism for enabling a user to apply air pressure to the pneumatic piston and cylinder mechanism to move said piston rod outwardly and thereby pull said loop attached to said pelvic traction belt toward the foot end of said device thereby to place traction with said pelvic traction belt on the lumbar region of the back of the user while the user is held by said chest strap to said upper surface of said upper hollow part.

4. The pneumatic lumbar traction device of claim 1 wherein said first clip has a slot on each side thereof an elongate bar extends through said slots and said strap is received around said bar for being pulled until locked by said bar to said first clip on said strap.

5. The pneumatic lumbar traction device of claim 1 wherein said end portions of said chest belt have a length between 8 and 12 inches.

6. The pneumatic lumbar traction device of claim 1 wherein said chest belt end portions have a length of about 11 inches.

7. The pneumatic lumbar traction device of claim 1 wherein the overall length of said chest belt is between 46 and 52 inches.

8. The pneumatic lumbar traction device of claim 1 wherein said length of said chest belt is about 50 inches.

9. The pneumatic lumbar traction device of claim 1 wherein the width of said chest belt end portions 28 is between 5 and 7 inches.

10. The pneumatic lumbar traction device of claim 1 wherein the width of said chest belt end portions is about 6 inches.

11. The pneumatic lumbar traction device of claim 1 wherein each strap on each chest belt has an inner end that is fixed by stitching to the chest belt.

12. The pneumatic lumbar traction device of claim 1 wherein each strap on said chest belt has a first male clip slidable on said first strap for being clipped in a second female clip fixed to an outer surface of an opposite end portion.

13. The pneumatic lumbar traction device of claim 12 wherein said female clips are mounted to rectangular tabs 34 which are fixed by stitching to the chest belt.

14. The pneumatic lumbar traction device of claim 1 wherein said straps on said chest belt have a length of between 13 and 20 inches.

15. The pneumatic lumbar traction device of claim 12 wherein said straps on said chest belt have a length between 15 and 18 inches from an inner end of said strap to said male clip at said outer end and are adjustably fixed in a particular position, like an airplane seat belt.

16. The pneumatic lumbar traction device of claim 13 wherein the distance between an inner edge of each tab to an outer edge of each end portion is between 15 and 17 inches.

17. The pneumatic lumbar traction device of claim 16 wherein said distance is about 16 inches.

18. The pneumatic lumbar traction device of claim 13 wherein the width of each strap and tab 34 is between 1 and 2 inches.

19. The pneumatic lumbar traction device of claim 18 wherein said width is about 1.5 inches.

20. The pneumatic lumbar traction device of claim 19 wherein the spacing between said straps and tabs is between 1 and 2 inches.

21. The pneumatic lumbar traction device of claim 20 wherein said spacing is about 1.5 inches.

22. The pneumatic lumbar traction device of claim 1 wherein said chest belt has a mid portion having a width between 8 and 10 inches.

23. The pneumatic lumbar traction device of claim 22 wherein said width is about 9 inches wide.

24. The pneumatic lumbar traction device of claim 1 wherein the pelvic traction belt end portions have a length between 8 and 12 inches.

25. The pneumatic lumbar traction device of claim 24 wherein said length is about 11 inches.

26. The pneumatic lumbar traction device of claim 1 wherein the overall length of said pelvic traction belt 54 is between 46 and 52 inches.

27. The pneumatic lumbar traction device of claim 26 wherein said length is about 50 inches.

28. The pneumatic lumbar traction device of claim 1 wherein the width of said pelvic traction belt the end portions 56 and 57 is between 5 and 7 inches.

29. The pneumatic lumbar traction device of claim 28 wherein said width is about 6 inches.

30. The pneumatic lumbar traction device of claim 1 wherein each strap on said pelvic traction belt has an inner end that is fixed by stitching to the pelvic traction belt.

31. The pneumatic lumbar traction device of claim 30 wherein each strap has a male clip fixed to an outer end thereof for being clipped in one of two female clips fixed to said pelvic traction belt.

32. The pneumatic lumbar traction device of claim 31 wherein said female clips 60, 61 are mounted to rectangular tabs which are fixed by stitching, to the pelvic traction belt.

33. The pneumatic lumbar traction device of claim 1 wherein said straps on said pelvic traction belt have a length of between 13 and 20 inches.

34. The pneumatic lumbar traction device of claim 33 wherein said length is 15 to 18 inches from the inner end of said strap to the male clip at the outer end and are adjustably fixed in a particular position, like an airplane seat belt.

35. The pneumatic lumbar traction device of claim 32 wherein the distance from an inner edge of each tab to an outer edge of a respective end portion of said pelvic traction belt is between 15 and 17 inches.

36. The pneumatic lumbar traction device of claim 35 wherein said distance is about 16 inches.

37. The pneumatic lumbar traction device of claim 1 wherein the width of each strap and each tab on said pelvic traction belt is between 1 and 2 inches.

38. The pneumatic lumbar traction device of claim 37 wherein said width is about 1.5 inches.

39. The pneumatic lumbar traction device of claim 37 wherein the spacing between said straps and tabs is between 1 and 2 inches.

40. The pneumatic lumbar traction device of claim 39 wherein said spacing is about 1.5 inches.

41. The pneumatic lumbar traction device of claim 1 wherein said pelvic traction belt has the mid portion 64 having a width between 8 and 10 inches.

42. The pneumatic lumbar traction device of claim 41 wherein said width is about 9 inches wide.

43. For use in a lumbar traction device having an upper surface with spaced apart elongate strips of hook or loop material on said upper surface, a generally elongate chest belt having opposite end portions with a strap fixed on each end portion with a first clip on said strap and a mating second clip fixed on the opposite end portion, each strap, after said mating clips are fixed together, being capable of being pulled through said first clip thereby to tighten it on the first clip against said fixed mating second clip thereby to tighten the chest belt around a users chest, and an outer surface of said chest belt having a loop or hook like texture for engaging and being releasably fixed to said strips of hook or loop material.

44. For use in a lumbar traction device having a lubricious upper surface and a bar or lug fixed to a piston rod extending from a foot end of the device for engaging a loop fixed to and extending transversely of a pelvic traction belt, a pelvic traction belt adapted to be received around the pelvic area of a user and having said loop fixed thereto and extending outwardly transversely of the pelvic traction belt toward said foot end of said device and said belt having opposite end portions with a strap fixed on each end portion with a first clip on said strap and a mating second clip fixed on the opposite end portion, each strap, after said mating clips are fixed together, being capable of being pulled through said first clip thereby to tighten it on the first clip against said fixed mating second clip thereby to tighten the pelvic traction belt around a users pelvic area.

\* \* \* \* \*